United States Patent [19]
Nadler et al.

[11] Patent Number: 5,977,179
[45] Date of Patent: Nov. 2, 1999

[54] NITRO-BENZAMIDES USEFUL AS ANTI-ARRHYTHMIC AGENTS

[75] Inventors: Guy Marguerite Marie Gerard Nadler, Rennes; Michel Jean Roger Martin, St. Gregoire, both of France

[73] Assignee: SmithKline Beecham p.l.c., Brentford, United Kingdom

[21] Appl. No.: 08/836,019

[22] PCT Filed: Oct. 24, 1995

[86] PCT No.: PCT/EP95/04203

§ 371 Date: Jul. 2, 1997

§ 102(e) Date: Jul. 2, 1997

[87] PCT Pub. No.: WO96/13479

PCT Pub. Date: May 9, 1996

[30] Foreign Application Priority Data

Oct. 26, 1994 [FR] France .................................. 94 12806

[51] Int. Cl.[6] ....................... A61K 31/165; C07C 233/65
[52] U.S. Cl. ........................................... 514/619; 564/166
[58] Field of Search ............................ 514/619; 564/166, 564/142

[56] References Cited

U.S. PATENT DOCUMENTS 5,208,252  5/1993  Russell et al. ........................... 514/438

FOREIGN PATENT DOCUMENTS

A0285284  10/1988  European Pat. Off. ..
A3242344  5/1984  Germany .

OTHER PUBLICATIONS

Biochem J., Sim, et al. "Metabolics of procainamide and practolol inhibit complement components C3 and C4". p. 324, 1988.

*Primary Examiner*—Shailendra Kumar
*Attorney, Agent, or Firm*—Mary E. McCarthy; Stepehn Venetianer; Charles M. Kinzig

[57] ABSTRACT

A compound of formula (I), or a salt thereof, or a solvate thereof, wherein Ar represents substituted or unsubstituted aryl, wherein the optional substituents are selected from alkyl, hydroxy or alkoxy or, if attached to adjacent carbon atoms any two substituents together with the carbon atoms to which they are attached may form a fused heterocyclic ring of five to six atoms wherein one, two or three of the said atoms are oxygen or nitrogen; A represents a $C_{1-4}$n-alkylene group wherein each carbon is optionally substituted by 1 or 2 $C_{1-6}$-alkyl groups; $R_1$ represents hydrogen, alkyl, alkenyl or cycloalkyl; one or two of the group of $R_2$, $R_3$ and $R_4$ represents nitro the remaining members of the group of $R_2$, $R_3$ and $R_4$ represent hydrogen; X represents a —CO—NH— moiety; and Z represents $C_{2-4}$n-alkylene group wherein each carbon is optionally substituted 1 or 2 $C_{1-6}$alkyl groups; a process for preparing such compounds, pharmaceutical compositions comprising such compounds and the use of such compounds in medicine.

3 Claims, No Drawings

NITRO-BENZAMIDES USEFUL AS ANTI-ARRHYTHMIC AGENTS

This application is a 371 of PCT/EP95/04203, filed Oct. 24, 1995.

The invention relates to certain novel compounds, to pharmaceutical compositions containing such compounds, to a process for the preparation of such compounds and to the use of such compounds as active therapeutic agents.

Anti-arrhythmic agents are classified according to their electrophysiological effects on the cardiac cell (Vaugham-Williams, 1970, 1989): class I agents block the fast sodium current, class II agents are beta-adrenergic blockers, class III agents block potassium currents, class IV agents block the calcium current, and class V agents are specific sinus node inhibitors.

A majority of ventricular and atrial arrhythmias are related to reentrant circuit. The prolongation of myocardial refractoriness within or surrounding such a reentrant circuit is a potential mechanism for the management of cardiac arrhythmias.

Because class III antiarrhythmic agents block cardiac potassium currents, they prolong the repolarisation process and increase refractoriness. Consequently class III agents represent the most specific class to treat reentrant arrhythmias.

However, due to their mechanism of action, i.e. a concentration dependent increase in the cardiac action potential duration, higher doses of class III antiarrhydimic agents may trigger arrhythmias. Such arrhythmias, called Torsade de Pointe represent the main adverse effect for all pure class III compounds currently in development.

European Patent Application, Publication Number 0 245 997 discloses certain aminoethylsulphoanilides which are stated to have pure class III antiarrhythmic properties.

It has now been discovered that certain novel substituted 4-nitrobenzamide derivatives induce a self-limiting increase of the cardiac action potential duration, related to a dual blockade of cardiac potassium and calcium channels. Consequently, they are considered to be useful anti-arrhythmic agents having an improved pharmacological profile over pure class III anti-arrhythmic agents, in particular they are considered to show a low proarrhythmic potential and readily restore the contractile function of the ischaemic myocardium. They are considered to be particularly useful for the treatment of atrial or ventricular cardiac arrhythmias.

Accordingly, the invention relates to a compound of formula (I):

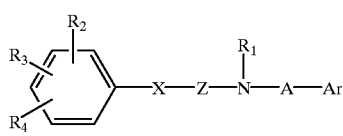

(I)

or a salt thereof, or a solvate thereof, wherein
Ar represents substituted or unsubstituted aryl, wherein the optional substituents are selected from alkyl, hydroxy or alkoxy or, if attached to adjacent carbon atoms any two substituents together with the carbon atoms to which they are attached may form a fused heterocyclic ring of five to six atoms wherein one, two or three of the said atoms are oxygen or nitrogen;
A represents a $C_{1-4}$ n-alkylene group wherein each carbon is optionally substituted by 1 or 2 $C_{1-6}$ alkyl groups;
$R_1$ represents hydrogen, alkyl, alkenyl or cycloalkyl;
one or two of the group of $R_2$, $R_3$ and $R_4$ represents nitro the remaining members of the group of $R_2$, $R_3$ and $R_4$ represent hydrogen;
X represents a —CO—NH— moiety; and
Z represents $C_{2-4}$ n-alkylene group wherein each carbon is optionally substituted by 1 or 2 $C_{1-6}$ alkyl groups.

Suitable substituents for Ar are 1, or favourably, 2 alkoxy groups, especially methoxy groups, the substituents favourably being attached at the 3- and 4-positions relative to the point of attachment of Ar to variable A.

Preferably, Ar represents 3,4-dimethoxyphenyl Suitably, A represents an unsubstituted $C_{1-4}$ n-alkylene group.

Preferably, A represents —$CH_2$—$CH_2$—.

When $R_1$ is alkyl it is preferably $C_{2-6}$ alkyl such as $C_2$- alkyl, $C_3$ alkyl, $C_4$ alkyl $C_5$ alkyl or $C_6$ alkyl.

In one aspect, $R_1$ is alkylene or cycloalkyl.

Preferably, $R_1$ is hydrogen.

Suitably, any one of $R_2$, $R_3$ and $R_4$ represents nitro and the remaining members of the group of $R_2$, $R_3$ and $R_4$ represent hydrogen.

Preferably, $R_2$ represents 4-nitro.

Preferably, $R_3$ and $R_4$ each represents hydrogen.

Suitably, Z represents an unsubstituted $C_{2-4}$ n-alkylene group.

Suitably, Z represents $CH_2CH_2CH_2$.

A particularly preferred compound of formula is N-[3-[[2-(3,4-dimethoxyphenyl)ethyl]amino]propyl]-4nitro benzamide or a salt thereof, such as a hydrochloride salt, or a solvate thereof.

As used herein unless otherewise stated, the term "alkyl" includes straight or branched chain alkyl groups having from 1 to 12, favourably 1 to 6 carbon atoms and shall include such alkyl groups when forming part of other groups such as alkoxy or arylalkyl groups.

As used herein, the term "alkylene" includes straight or branched chain alkylene groups having from 2 to 12, favourably 2 to 6 carbon atoms.

As used herein, the term "cycloalkyl" includes $C_{3-8}$ cycloalkyl groups, favourably $C_{5-6}$ carbon groups.

As used herein, unless otherwise stated, the term "aryl" includes phenyl and naphthyl, preferably phenyl.

As used herein, unless otherwise stated, "halogen" includes fluorine, chlorine or bromine.

As used herein, the term "cardiac arrhythmia" relates to any variation from the normal rhythm of heart beat, including, without limitation, sinus arrhythmia, premature heartbeat, heartblock, fibrillation, flutter, tachycardia, paroxysmal tachycardia and premature ventricular contractions.

The compounds of formula (I) may possess a chiral carbon atom (for example when Z represents a branched alkylene group and may therefore exist in more than one stereoisomeric form The invention extends to any of the stereoisomeric forms, including enantiomers of the compounds of formula (I) and to mixtures thereof, including racemates. The different stereoisomeric forms may be separated or resolved one from the other by conventional methods or any given isomer may be obtained by conventional stereospecific or asymmetric syntheses.

The pharmaceutically acceptable salts of the compounds of formula (I) include acid addition salts with pharmaceutically acceptable mineral acids such as hydrochloric, hydrobromic, boric, phosphoric, sulphuric and pharmaceutically acceptable organic acids such as acetic, tartaric, maleic, citric, succinic, benzoic, ascorbic, methanesulphonic, α-keto-glutaric, α-glycerophosphoric, and glucose-1-phosphoric acids. Preferably the acid addition salt is a hydrochloride.

Pharmaceutically acceptable salts include pharmaceutically acceptable N-oxides, and the invention extends to these.

The compounds of the formula (I) and their salts may also form solvates, especially pharmaceutically acceptable solvates, such as hydrates, and the invention extends to these, and especially to the pharmaceutically acceptable solvates.

The salts and/or solvates of the compounds of the formula (I) which are not pharmaceutically acceptable may be useful as intermediates in the preparation of pharmaceutically acceptable salts of compounds of formula (I) or the compounds of the formula (I) themselves, and as such form an aspect of the present invention.

A compound of formula (I), or a salt thereof, or a solvate thereof, may be prepared by reacting a compound of formula (II):

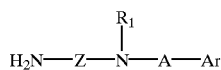

(II)

wherein A, Ar, $R_1$ and Z are as defined in relation to formula (I), with a compound of formula (III):

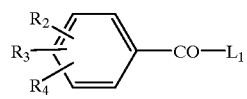

(III)

wherein $R_2$, $R_3$ and $R_4$ are as defined in relation to formula (1) and $L_1$ represents a leaving group; and thereafter, if required, carrying out one or more of the following optional steps:

(i) converting a compound of formula (I) into a further compound of formula (I);

(ii) preparing a salt of the compound of formula (I) and/or a pharmaceutically acceptable solvate thereof.

Compounds of formula (III) are known, commercially available compounds.

The reaction between the compounds of formulae (II) and (III) may be carried out in any suitable inert solvent, such as dichloromethane, in the presence of a base, usually an organic base, for example triethylamine, at a temperature which provides a suitable rate of formation of the required product, generally at a low to ambient temperature, preferably ambient.

A preferred leaving group $L_1$ is a halogen atom, such as a chlorine atom.

The compounds of formula (II) are known compounds and may be prepared by the method described in Offenlegungsschrift 2345423.

The compounds of formula (II) may also be prepared by reducing a compound of formula (IV):

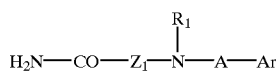

(IV)

wherein A, Ar and $R_1$ are as defined in relation to the compound of formula (1) and $Z_1$ represents $C_{1-3}$ n-alkylene group wherein each carbon is optionally substituted by a $C_{1-6}$ alkyl group.

The reduction of the compounds of formulae (IV) may be carried out using conventional reducing agents and conditions, for example by using a metal hydride reducing agent, such as lithium aluminium hydride, in an aprotic solvent, such as tetrahydrofuran or diethyl ether or mixtures thereof, at a temperature which provides a suitable rate of formation of the required product, generally at an elevated temperature and conveniently at the reflux temperature of the solvent.

The compounds of formula (IV) may be prepared by reacting a compound of formula (V):

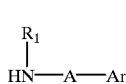

(V)

wherein A, Ar and $R_1$ are as defined in relation to the compound of formula (I), with a compound of formula (VI):

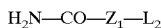

(VI)

wherein $Z_1$ is as defined in relation to the compound of formula (IV) and $L_2$ represents a leaving group.

The reaction between the compounds of formulae (V) and (VI) is carried out in an aprotic solvent, such as acetonitrile, at a temperature which provides a suitable rate of formation of the required product, generally at an elevated temperature and conveniently at the reflux temperature of the solvent; preferably the reaction is carried out in the presence of base, usually an organic base such as a trialkylamine, for example triethylamine or a complex such as potassium fluoride on celite (Takashi Ando, Junko Yamawaki, Chemistry Letters, 1979, p.45).

A preferred leaving group $L_2$ is a halogen atom, such as a chlorine atom.

The compounds of formula (V) are known, commercially available compounds.

The compounds of formula (VI) are known compounds or they are prepared using methods analogous to those used to prepare known, commercially available compounds.

In a further aspect the invention provides a process for the preparation of a compound of formula (I), which process comprises demethylating a compound of formula (VII):

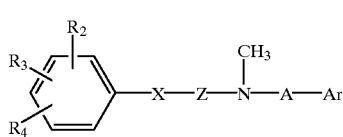

(VII)

wherein A, Ar, $R_2$, $R_3$, $R_4$ X and Z are as defined in relation to the compounds of formula (I); and thereafter, as required, converting any —NH— moiety so formed into a group $NR_5$ wherein $R_5$ represents $C_{2-6}$ alkyl, an alkenyl or a cycloalkyl group.

The demethylation of the compounds of formula (VII) may be affected by using any conventional demethylation process, for example by use of methods disclosed in J. Org. Chem., 1975, 40, 1850, ibid, 1984, 49, 2081 or those methods disclosed in Synthesis 1991, 318.

The conversion of any —NH— moiety into a group $NR_5$ wherein $R_5$ represents a $C_{2-6}$ alkyl, an alkenyl or a cycloalkyl group may be carried out using conventional alkylation, alkenylation or cycloalkylation methods, by use of the appropriate alkylhalide, alkenylhalide or cycloalkylhalide, suitably an iodide, in the presence of a base such as potassium bicarbonate in an aprotic solvate such as tetrahrydrofuran.

In a further aspect the invention provides a compound of formula (VII) or a salt thereof or a solvate thereof as an intermediate.

A compound of formula (I), or a salt thereof, or a solvate thereof, may also be prepared by reacting a compound of formula (VIII):

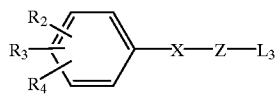

(VIII)

wherein $R_2$, $R_3$ $R_4$ X and Z are as defined in relation to formula (I) and $L_3$ is a leaving group, such as a halogen, with a compound of formula (IX):

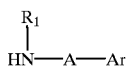

(IX)

wherein A, Ar, $R_1$ are as defined in relation to formula (I); and thereafter, if required, carrying out one or more of the following optional steps:
  (i) converting a compound of formula (I) into a further compound of formula (I);
  (ii) preparing a salt of the compound of formula (I) and/or a pharmaceutically acceptable solvate thereof.

The reaction between the compounds of formulae (VIII) and (IX) may be carried out in any suitable inert solvent, such as dichloromethane, in the presence of a base, usually an organic base, for example triethylamine, at a temperature which provides a suitable rate of formation of the required product, generally at an elevated temperature, such as the reflux temperature of the solvent.

A suitable value for $L_3$ is chlorine.

A compound of formula (VIII) may be prepared by reaction between a compound of above defined formula (III) and a compound of formula (X):

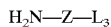 $H_2N\text{—}Z\text{—}L_3$ (X)

wherein Z is as defined in relation to formula (I) and $L_3$ is as defined in realtion to formula (VII).

The reaction between the compounds of formulae (III) and (X) may be carried under conventional acylation conditions for example in an inert solvent, such as dichloromethane, in the presence of a base, usually an organic base, for example triethylamine, at a temperature which provides a suitable rate of formation of the required product, generally at a low to ambient temperature, preferably at ambient temperature.

The compounds of formula (X) are known, commercially available compounds.

A suitable conversion of one compound of formula (I) into a further compound of formula (I) involves the interconversion of variable $R_1$ in the compounds of formula (I), for example the conversation of compounds wherein $R_1$ is H into compounds of formula (I) wherein $R_1$ represents alkyl, suitably $C_{2-6}$ alkyl, alkenyl or cycloalkyl or the above mentioned conversation of compounds wherein $R_1$ is methyl into compounds wherein $R_1$ is hydrogen, $C_{2-6}$ alkyl, alkenyl or cycloalkyl.

It will be appreciated that in any of the abovementioned reactions and conversions any reactive group in the substrate molecule may be protected, according to conventional chemical practice. The methods of formation and removal of such protecting groups are those conventional methods appropriate to the molecule being protected.

As mentioned above the compounds of the invention are indicated as having useful therapeutic properties: The present invention accordingly provides a compound of formula (I), or a pharmaceutically acceptable salt thereof and/or a pharmaceutically acceptable solvate thereof, for use as an active therapeutic substance.

More particularly, the present invention provides a compound of formula (), or a pharmaceutically acceptable salt thereof and/or a pharmaceutically acceptable solvate thereof, for use in the treatment of and/or prophylaxis of arrhythmia, especially cardiac arrhythmia such as ventricular arrhythmia, and also ischaemic rhythm disorders.

A compound of formula (I), or a pharmaceutically acceptable salt thereof and/or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising a compound of the general formula (I), or a pharmaceutically acceptable salt thereof, or a pharmaceutically acceptable solvate thereof, and a pharmaceutically acceptable carrier therefor.

A compound of formula (I) or a pharmaceutically acceptable salt thereof and/or a pharmaceutically acceptable solvate thereof is normally administered in unit dosage form.

An amount effective to treat the disorder hereinbefore described depends upon such factors as the efficacy of a compound of formula (I), the particular nature of the pharmaceutically acceptable salt or pharmaceutically acceptable solvate chosen, the nature and severity of the disorders being treated and the weight of the mammal However, a unit dose will normally contain 0.1 to 500 mg for example 2 to 50 mg, of the compound of the invention. Unit doses will normally be administered once or more than once a day, for example 2,3,4,5 or 6 times a day, more usually 2 to 4 times a day, such that the total daily dose is normally in the range, for a 70 kg adult of 0.1 to 2500 mg, more usually 1 to 1000 mg, for example 1 to 200 mg, that is in the range of approximately 0.02 to 3 mg/kg/day, more usually 0.1 to 3 mg/kg/day, for example 0.15 to 2 mg/kg/day.

At the above described dosage range, no toxicological effects are indicated for the compounds of the invention.

In such treatment, the compound may be administered by any suitable route, e.g. by the oral, parenteral or topical routes. For such use, the compound will normally be employed in the form of a pharmaceutical composition in association with a human or veterinary pharmaceutical carrier, diluent and/or excipient, although the exact form of the composition will naturally depend on the mode of administration.

Compositions are prepared by admixture and are suitably adapted for oral, parenteral or topical administration, and as such may be in the form of tablets, capsules, oral liquid preparations, powders, granules, lozenges, pastilles, reconstitutable powders, injectable and infusable solutions or suspensions, suppositories and transdermal devices. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

Solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the active compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the active compound is suspended in the vehicle instead of being dissolved and sterilised by exposure to ethylene oxide before suspending in the sterile vehicle. Advantageously, a surfactant or wetting agent is included in the composition to facilitate uniform distribution of the active compound For topical administration, the composition may be in the form of a transdermal ointment or patch for systemic delivery of the compound and may be prepared in a conventional manner, for example, as described in the standard textbooks such as 'Dermatological Formulations'—B. W. Barry (Drugs and the Pharmaceutical Sciences—Dekker) or Harrys Cosmeticology (Leonard Hill Books).

In addition such compositions may contain further active agents such as anti-hypertensive agents and diuretics.

As is common practice, the compositions will usually be accompanied by written or printed directions for use in the medical treatment concerned.

As used herein the term 'pharmaceutically acceptable' embraces compounds, compositions and ingredients for both human and veterinary use: for example the term 'pharmaceutically acceptable salt' embraces a veterinarily acceptable salt.

The present invention further provides a method for the treatment and/or prophylaxis of arrhythmia, especially cardiac arrhythmia such as ventricular arrhythmia, and also ischemic rhythm disorders in a human or non-human mammal which comprises administering an effective, non-toxic, amount of a compound of the general formula (I), or a pharmaceutically acceptable salt thereof and/or a pharmaceutically acceptable solvate thereof to a human or non-human mammal in need thereof.

Conveniently, the active ingredient may be administered as a pharmaceutical composition hereinbefore defined, and this forms a particular aspect of the present invention.

In the treatment and/or prophylaxis of arrhythmia and/or ischaemic arrhythmia disorders the compound of the general formula (I), or a pharmaceutically acceptable salt thereof and/or a pharmaceutically acceptable solvate thereof, may be taken in doses, such as those described above.

Similar dosage regimens are suitable for the treatment and/or prophylaxis of non-human mammals.

In a further aspect the present invention provides the use of a compound of formula (I), or a pharmaceutically acceptable salt thereof and/or a pharmaceutically acceptable solvate thereof, for the manufacture of a medicament for the treatment of arrhythmia, especially cardiac arrhythmia such as ventricular arrhythmia, and also ischaemic rhythm disorders.

No toxicological effects are indicated when a compound of formula (I) or a pharmaceutically acceptable salt thereof and/or a pharmaceutically acceptable solvate thereof is administered in the above mentioned dosage ranges.

The following Descriptions and Examples illustrate the invention but do not limit it in any way.

DESCRIPTION 1

3-[[2-(3,4-Dimethoxyphenyl)ethyl]methylamino] propanamide

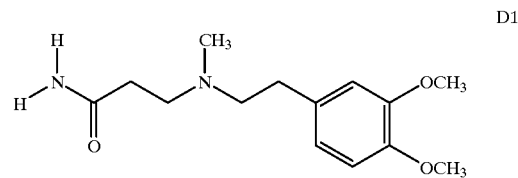

D1

6.42 g (60 mmol) 3-Chloropropanamide, 5.85 g (30mmol) N-methyl-3,4-dimethoxybenzeneethanamine and 7.7 g (75 mmol) triethylamine in 100 ml acetonitrile were stirred under reflux for 18 hours. The reaction mixture was concentrated in vacuo and the residue purified by chromatography on silicagel using methylene chloride/methanol: 92/8 to yield 5.12 g (64.1%) of the desired compound as an orange oil.

$^1$H NMR (CDCl$_3$) δ=2.40 (s,3H,NCH$_3$); 2.46 (t,2H,J= 5.9Hz,CH2); 2.74–2.79 (m,6H,3CH$_2$); 3.85 and 3.87 (2s, 6H,2CH$_3$O) ; 6.70–6.78 (m,3H,3Ar); 7.71 (broad band,2H, exch D$_2$O,NH$_2$) ppm.

DESCRIPTION 2

N-[2-(3,4-dimethoxyphenyl)ethyl]-N-methyl-1,3-propanediamine

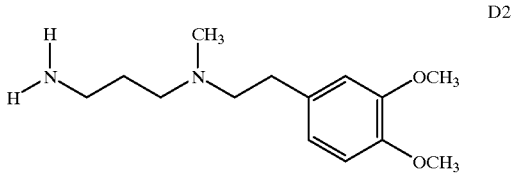

D2

1.5 g (5.6 mmol) 3-[[2-(3,4-Dimethoxyphenyl)ethyl] methylamino]propanamide (D1) in dry tetrahydrofuran were added dropwise to a suspension of 0.64 g (1.7 mmol) lithium aluminium hydride in 20 ml dry diethylether whilst stirring. The mixture was heated under reflux for 2 hours then cooled with a bath of ice water before carefully adding dropwise 0.65 ml water, 0.65 ml 15% aqueous NaOH, then 1.95 ml water. The mixture was dried over MgSO$_4$, concentrated in vacuo and the residue was purified twice by chromatography on basic alumina using methylene chloride/methanol: 95/5 then methylene chloride/methanol/30% aqueous ammonia: 90/10/0.1 to yield 0.86 g (60.8%) of the desired compound.

$^1$H NMR (CDCl$_3$) δ=1.65 (m,2H,CH$_2$); 2.15 (broad band, 2H,exch D$_2$O,NH$_2$); 2.30 (s,3H,NCH$_3$); 2.47 (t,2H,J'=7.4Hz,CH2) ; 2.53–2.79 (m,6H,3CH$_2$) ; 3.85 and 3.87 (2s,6H,2CH$_3$O); 6.71–6.82 (m,3H,3Ar) ppm.

DESCRIPTION 3

N-(3-Chloropropyl)-4-nitrobenzamide

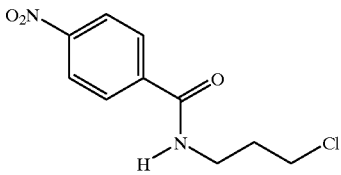

A solution of 6.43 g (49 mmol) 3-chloropropylamine and 13.6 ml (98 mmol) triethylamine in 220 ml methylene chloride was cooled by an ice bath and 9 g (48.5 mmol) 4-nitrobenzoyl chloride were added fractionwise. After one hour stirring at room temperature the organic phase was washed twice with water, dried over MgSO$_4$ and concentrated in vacuo to afford 10.68 g (91%). of beige crystals. $^1$H NMR was consistent with the desired structure.

EXAMPLE 1

N-[3-[[2-(3,4-Dimethoxyphenyl)ethyl]methylamino] propyl]4-nitrobenzamide hydrochloride

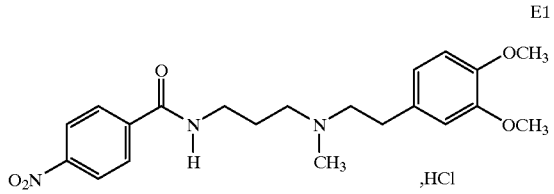

E1

800 mg (3.17 mmol) N-[2-(3,4-Dimethoxyphenyl)ethyl]-N-methyl-1,3-propanediamine (D2), 630 mg (3.33 mmol) 4-nitro benzoyl chloride and 0.35 g (3.49 mmol) triethylamine in 30 ml methylene chloride were stirred for 2 hours at room temperature. The mixture was washed with water, dried over MgSO$_4$ and concentrated in vacuo. The residue was purified twice by chromatography on silicagel using methylene chloride/methanol: 97/3 then 94/6 yielding 700 mg (55%) of the desired compound as a base. The compound was salified in methylene chloride by adding a solution of hydrochoric acid in diethyl ether yielding 594 mg (43%) of the desired compound as a yellow solid: mp=80–90° C.

$^1$H NMR (DMSO-d$_6$) δ=2.00 (m,2H,CH$_2$); 2.79 (s,3H, NCH$_3$); 2.90 (m,2H,CH$_2$); 2.95 (m,2H,CH$_2$); 3.20 (m,2H, CH$_2$); 3.35 (m,2H,CH$_2$); 3.72 and 3.74 (2s,6H,2CH$_3$O); 6.80–6.96 (m,3H,Ar); 8.12 (d,2H,J=7.9Hz,Ar) ; 8.33 (d,2H, J=7.9Hz,Ar); 9.05 (broad band,1H,exch D$_2$O,NH); 10.45 (broad band,1H,exch D$_2$O,NH) ppm.

EXAMPLE 2

N-[3-[[2-(3,4-Dimethoxyphenyl)ethyl]amino] propyl]-4-nitro benzamide hydrochloride

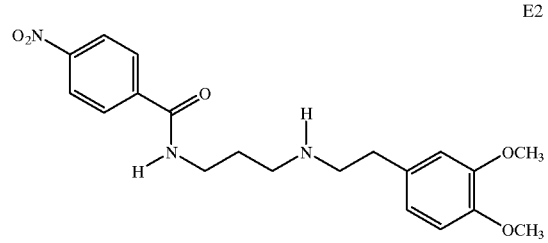

E2

A solution of 10.62 g (44 mmol) N-(3-chloropropyl)-4-nitrobenzamide (D3), 8.1 g (45 mmol) homoveratrylamine and 6.26 ml triethylamine in 200 ml methylene chloride was refluxed for 48 h. The solvent was then concentrated in vacuo and the residue dissolved in water. The aqueous phase was first washed with methylene chloride, then made basic with aqueous NaOH and finally extracted twice with methylene chloride. This second organic phase was dried over MgSO$_4$ and concentrated in vacuo affording 12 g of a crude residue. This residue was purified by chromatography on silicagel using CH$_2$Cl$_2$/MeOH/NH$_4$OH: 85/10/5 to afford 4.4 g of the title compound as an yellow oil (free base).

This compound was dissolved in methanol and acidified by a solution of anhydrous hydrogen chloride in diethyl ether, affording after drying 4.4 g of the title compound as light beige crystals. mp.: 141–2° C.

$^1$H NMR (DMSO-d$_6$) δ=1.93 (m, 2H, CH$_2$); 2.89–3.16 (m, 6H, 3xCH$_2$); 3.40 (m, 2H, CH$_2$); 3.72 and 3.75 (2s, 6H, 2xOCH$_3$); 6.74–6.91 (m, 3H, Ar); 8.12 (d, 2H, J=8.6Hz, Ar); 8.32 (d, 2H, J=8.6Hz, Ar); 9.12 (broad band, 2H, exch. D$_2$O, NH$_2$+); 9.15 (t, 1H, exch. D$_2$O, NH) ppm.

PHARMACOLOGICAL DATA

Methodology

Guinea pigs (300–350 g) were anesthetized by intravenous injection of sodium pentobarbital (60 mg/kg). After thoracotomy the heart was rapidly excised and placed in oxygenated Tyrode solution. Papillary muscles were removed from the right ventricle. Preparations were then fixed to the silastic base of a 5 ml organ bath and superfused with oxygenated Tyrode solution maintained at 37±1° C. The modified Tyrode solution (pH 7.35) contained the following (mM): NaCl 125, KCl 4.0, $MgCl_2$ 0.5, $CaCl_2$ 1.8, $NaHCO_3$ 24, $NaH_2PO_4$ 0.9 and glucose 5.5. The solution was equilibrated with a gas mixture of 95% $O_2$-5% $CO_2$. After a stabilisation period (at least 1 h), transmembrane action potentials were recorded with conventional microelectrodes (10 MOhm) connected to a high input impedance amplifier (BIOLOGIC VF 180). External stimuli were delivered to the preparation with bipolar platinum electrodes placed at one end of the muscle. The pulse duration was 1 ms and the amplitude was twice threshold. The basic cycle length was 1000 ms (PULSAR 6i stimulator). The signals were monitored on a storage oscilloscope (GOULD 1602) and simultaneously recorded on a digital tape recorder (BIOLOGIC DTR 1200) for further analysis. Measurements were made of action potential amplitude (APA) and action potential durations at 30 and 90% repolarization (APD30 and APD90 respectively). Recordings were made after 30 min of equilibration for each concentration. Only recordings in which the same impalement was maintained throughout the entire experiment were used for analysis.

We claim:

1. A compound which is N-[3-[[2-(3,4-dimethoxyphenyl) ethyl]amino]propyl]-4-nitro benzamide; or a salt thereof, or a solvate thereof.

2. A pharmaceutical composition comprising a compound according to claim 1, or a pharmaceutically acceptable salt thereof and/or a pharmaceutically acceptable solvate thereof, and a pharmaceutically acceptable carrier.

3. A method for the treatment and/or prophylaxis of arrhythmia and ischaemic rhythm disorders in a human or non-human mammal which comprises administering an effective, non-toxic, amount of a compound according to claim 1, or a pharmaceutically acceptable salt thereof and/or a pharmaceutically acceptable solvate thereof to a human or non-human mammal in need thereof.

* * * * *